(12) United States Patent
Heberlein et al.

(10) Patent No.: US 10,092,199 B2
(45) Date of Patent: Oct. 9, 2018

(54) MR IMAGING APPARATUS AND METHOD FOR GENERATING A PERFUSION IMAGE WITH MOTION CORRECTION

(71) Applicants: Siemens Healthcare GmbH, Erlangen OT (DE); The General Hospital Corporation, Boston, MA (US)

(72) Inventors: Keith Aaron Heberlein, Charlestown, MA (US); Himanshu Bhat, Cambridge, MA (US); Matthew Dylan Tisdell, Somerville, MA (US); Andre Jan Willem Van Der Kouwe, Woburn, MA (US)

(73) Assignees: Siemens Healthcare GmbH, Erlangen (DE); The General Hospital Corporation, Boston, MA (US)

( * ) Notice: Subject to any disclaimer, the term of this patent is extended or adjusted under 35 U.S.C. 154(b) by 755 days.

(21) Appl. No.: 14/676,011

(22) Filed: Apr. 1, 2015

(65) Prior Publication Data

US 2015/0272453 A1    Oct. 1, 2015

Related U.S. Application Data

(60) Provisional application No. 61/973,324, filed on Apr. 1, 2014.

(51) Int. Cl.
*A61B 5/026* (2006.01)
*A61B 5/055* (2006.01)
*G01R 33/563* (2006.01)
*G01R 33/567* (2006.01)
(Continued)

(52) U.S. Cl.
CPC ............ *A61B 5/0263* (2013.01); *A61B 5/055* (2013.01); *A61B 5/7207* (2013.01); *G01R 33/5676* (2013.01); *G01R 33/56366* (2013.01); *G01R 33/5616* (2013.01); *G01R 33/5618* (2013.01)

(58) Field of Classification Search
CPC ................ A61B 5/7207; A61B 5/0263; G01R 33/56366
See application file for complete search history.

(56) References Cited

U.S. PATENT DOCUMENTS

| | | |
|---|---|---|
| 6,271,665 B1 | 8/2001 | Berr et al. |
| 7,898,254 B2 | 3/2011 | Feinberg et al. |
| 8,203,340 B2 | 6/2012 | Pfeuffer |

(Continued)

OTHER PUBLICATIONS

D. A. Feinberg et al., Cerebral Blood Flow Imaging With 3D GRASE ASL Sequence Increases SNR and Shortens Acquisition Time, MAGNETOM Flash, 62-69 (Mar. 2009).

(Continued)

*Primary Examiner* — Giovanni Astacio-Oquendo
*Assistant Examiner* — Alvaro Fortich

(57) ABSTRACT

A magnetic resonance method and system are provided for generating real-time motion-corrected perfusion images based on pulsed arterial spin labeling (PASL) with a readout sequence such as a 3D gradient and spin echo (GRASE) image data acquisition block. The real-time motion correction is achieved by using a volumetric 3D EPI navigator that is provided during an intrinsic delay in the PASL sequence, which corrects for motion prospectively and does not extend the image data acquisition time as compared to a similar non-motion-corrected imaging procedure.

15 Claims, 4 Drawing Sheets

(51) Int. Cl.
 *A61B 5/00* (2006.01)
 *G01R 33/561* (2006.01)

(56) References Cited

U.S. PATENT DOCUMENTS

| | | | | |
|---|---|---|---|---|
| 2005/0083053 | A1* | 4/2005 | Foo | G01R 33/56308 |
| | | | | 324/306 |
| 2012/0169336 | A1* | 7/2012 | Leigh | A61B 5/055 |
| | | | | 324/309 |
| 2012/0293171 | A1* | 11/2012 | Dannels | G01R 33/56333 |
| | | | | 324/309 |
| 2013/0187649 | A1* | 7/2013 | Bhat | A61B 5/055 |
| | | | | 324/307 |

OTHER PUBLICATIONS

M.D. Tisdall et al., Volumetric Navigators for Prospective Motion Correction and Selective Reacquisition in Neuroanatomical MRI, Magnetic Resonance in Medicine, 68:389-99 (2012).

W.M. Luh et al., QUIPSS II with thin-slice TI1 periodic saturation: a method for improving accuracy of quantitative perfusion imaging using pulsed arterial spin labeling, Magnetic Resonance in Medicine, 41(6):1246-54 (1999).

\* cited by examiner

No Motion no correction correction

Motion no correction correction

MR IMAGING APPARATUS AND METHOD FOR GENERATING A PERFUSION IMAGE WITH MOTION CORRECTION

CROSS-REFERENCE TO RELATED APPLICATION(S)

The present application relates to and claims priority from U.S. Provisional Patent Application Ser. No. 61/973,324 filed Apr. 1, 2014, the disclosure of which is incorporated herein by reference in its entirety.

STATEMENT REGARDING FEDERALLY SPONSORED RESEARCH

The present invention was made with government support under Grants R21MH096559, R01HD071664, R21EB008547, R33DA026104, and P41RR014075 awarded by the National Institute of Health (NIH). The government has certain rights in the invention.

FIELD OF THE DISCLOSURE

The present disclosure relates to a method and a system for generating magnetic resonance images, and in particular to a method and a system for generating magnetic resonance 3D perfusion images with motion correction.

BACKGROUND INFORMATION

Magnetic resonance (MR) imaging is a known technology that can produce images of the inside of an examination subject without radiation exposure. In a typical MR imaging procedure, the subject is positioned in a strong, static, homogeneous base magnetic field B0 (having a field strength that is typically between about 0.5 Tesla and 3 Tesla) in an MR apparatus, so that the subject's nuclear spins become oriented along the base magnetic field. Radio-frequency (RF) excitation pulses are directed into the examination subject to excite nuclear magnetic resonances, and subsequent relaxation of the excited nuclear magnetic resonances can generate RF signals. Rapidly switched magnetic gradient fields can be superimposed on the base magnetic field, in various orientations, to provide spatial coding of the RF signal data. The RF signal data can be detected and used to reconstruct images of the examination subject. For example, the acquired RF signal data are typically digitized and stored as complex numerical values in a k-space matrix. An associated MR image can be reconstructed from the k-space matrix populated with such values using a multi-dimensional Fourier transformation.

Magnetic resonance can be used to produce images representing tissue perfusion, which refers to the delivery of oxygen and nutrients to tissues of a subject by means of blood flow. Perfusion studies allow an assessment to be made of in vivo organ functions such as, e.g., brain activity. In certain MR perfusion imaging techniques, a contrast agent that generates a signal detectable by magnetic resonance imaging is injected into a subject. Magnetic resonance image data are acquired at a time when the contrast agent has optimally flowed into the region or anatomy of interest. Since the contrast agent is injected into the vascular system of the subject, the appearance of the contrast agent in the magnetic resonance image is representative of blood flow in the region or anatomy of interest. Magnetic resonance perfusion techniques are particularly useful in the context of magnetic resonance images of the head, in particular the brain, wherein cerebral blood flow (CBF) is identified.

Another MR perfusion imaging technique uses "arterial spin labeling" (ASL) instead of injection of a contrast agent. In an ASL procedure, a spatially selective inversion or saturation of water protons in arterial blood is used to label or "tag" blood flowing into the region to be imaged. For brain perfusion imaging, this tagged region can be a slab in a lower portion of the head and/or neck area below the region to be imaged, from where blood flows up into the brain. When the labeled or tagged blood reaches the tissue within the imaging region, it attenuates the MR signal emanating from the perfused tissue following spatially-selective excitation of the region. "Subtraction" of a labeled image from a control image (i.e., one obtained without labeled/tagged blood in the imaged region) can provide a measure of the amount of tagged blood that flowed into the imaged tissue. This quantity is closely related to the local tissue perfusion. The image subtraction can be achieved, e.g., by performing a voxel-by-voxel subtraction of image intensity between a tagged image and an immediately preceding or subsequent control image. In ASL procedures, the imaged region or volume will thus have different magnetization histories arising from the tagged and control pulse sequences.

The difference in the MR signal intensity for labeled and control images is typically only a few percent of the tissue MR signal, and thus MR images based on ASL differences often suffer from the influence of image noise. In some ASL imaging procedures, many repetitions (e.g. 10-50) of the ASL data acquisitions are averaged to increase the signal-to-noise ratio (SNR). Such factors of imaging time and small signals can make ASL techniques prone to motion corruption and artifacts, which can accumulate when acquiring data for a plurality of images. ASL techniques and certain approaches for reducing noise effects are described, e.g., in U.S. Pat. No. 8,203,340 of Pfeuffer.

The use of 3D encoding in ASL imaging, e.g., using a 3D gradient and spin echo technique (GRASE), can provide higher SNR than conventional slice-by-slice methods. The higher SNR can be based on, e.g., the faster echo refocusing larger number of echoes in an echo train compared to conventional EPI techniques. Further, such 3D sequences facilitate simultaneous readout that can better image a particular extent of tagged blood perfusion over a region of interest as compared to a 2D approach, where slices are encoded sequentially and thus at different perfusion times. The use of 3D encoding in ASL imaging procedures is described, e.g., in D. A. Feinberg et al., Cerebral Blood Flow Imaging With 3D GRASE ASL Sequence Increases SNR and Shortens Acquisition Time, MAGNETOM Flash, 62-69 (March 2009). However, such high-resolution 3D MR imaging can still be susceptible to motion corruption. Thus, the potential benefits of a 3D ASL imaging procedure, for example, in evaluating stroke in a subject, can be mitigated by its sensitivity to patient head motion due to the associated segmented k-space acquisition and subtraction artifacts arising from successive acquisition of control and labeled (tagged) images within the scan.

So-called "navigator" sequences are additional RF pulses that can be used in MR imaging procedures to dynamically track anatomical motion. Navigator pulses are typically spin echo (SE) or gradient echo (GRE) sequences. Echo signals returned by a navigator can be used to correct for motion during certain types of image acquisition sequences. For example, the use of volumetric (3D) navigator sequences to correct for motion effects is described in M. D. Tisdall et al., Volumetric Navigators For Prospective Motion Correction And Selective Reacquisition In Neuroanatomical MRI, Magnetic Resonance in Medicine, 68:389-99 (2012). The approach of Tisdall et al. is limited to imaging pulse sequences where the magnetization history is the same for every acquired navigator, and when motion is detected the entire imaging volume is adapted (i.e. translated and/or rotated) accordingly, to compensate for the detected change in position. Such a navigator approach is not compatible with typical 3D GRASE sequences, in which the magnetization history changes depending on whether a particular sequence is in the labeling or control phase. For example, in the labeling phase of a 3D GRASE ASL sequence, an additional tagging step is inserted in the sequence. When motion occurs during the imaging procedure, the imaged volume should be adapted to compensate for the motion, whereas the tagged volume should not be adapted because it is typically below the brain in the neck where the major arteries can be labeled.

Accordingly, it would be desirable to have a system and method for imaging perfusion that addresses some of the shortcomings described above, including effective motion correction that can be done in real time.

SUMMARY OF EXEMPLARY EMBODIMENTS

Exemplary embodiments of the present disclosure can provide a magnetic resonance system for generating real-time (prospective) motion-corrected perfusion images based on pulsed arterial spin labeling (PASL). The MR system can provide prospective motion correction, for example, between the control and tagged sequences used in a PASL procedure, where the control and tagged sequences have different magnetization histories, in contrast to conventional navigator techniques that correct motion between images having the same magnetization history.

The system can include various components of a conventional MR system including, e.g., a strong magnet in a radio-frequency (RF) shielded measurement chamber configured to generate a, strong base magnetic field B0 (e.g. between 1 Tesla and 3 Tesla) and further configured to receive a portion of a subject body to be imaged (e.g., a head if perfusion images of the brain are being generated).

The MR system also includes a pulse generation unit, pulse sequence control unit, a radio-frequency amplifier, and one or more RF antennas, such as a body coil, that are further configured to generate and emit RF excitation pulses to excite nuclear spins. The MR system further includes magnetic gradient coils, which may be oriented along the three primary axes (x- y- and z-directions). Other or additional orientations of the magnetic gradient coils can be used in further embodiments. A gradient coil control unit can be provided to supply pulsed current to the magnetic gradient coils to generate transient gradient magnetic fields superimposed on the static base magnetic field B0. The gradient coil control unit can also communicate with the pulse sequence control unit, such that RF pulses and magnetic field gradients can be synchronized in various ways to provide spatially selective excitation and spatial encoding of RF signals.

One or more local coils can also be provided to detect RF signals emitted by the excited nuclear spins, which may also be detected by the RF antenna. A radio-frequency preamplifier and an acquisition unit can also be provided to amplify, process, and digitized the detected RF signals. In certain embodiments, a coil (e.g., a body coil) can be configured to both emit RF excitation pulses and receive RF signals emitted by nuclear spins, and an upstream transmission-reception diplexer can be provided to regulate the relaying of RF energy to/from the coil.

The MR system can further include an image processing unit configured to generate one or more images based on the RF signals that represent image data. Such images can be presented to a user via an operator console and/or be stored in a memory unit. A processor arrangement can be provided and configured to control various components of the MR system, e.g., based on programmed instructions. For example, the processor arrangement can be configured to control the pulse generation unit, pulse sequence control unit, the radio-frequency amplifier, and/or the gradient coil control unit to generate particular temporal sequences of RF pulses and magnetic field variations, and optionally to control other components such as the image processing unit, according to exemplary embodiments of the disclosure described herein.

In one embodiment, the system can be configured to perform motion-corrected perfusion MR imaging based on a flow-sensitive alternating inversion recovery (FAIR) approach, using first and second exemplary sequences of RF pulses. A pulse, as used in the present disclosure, can include a single pulse of RF energy or a particular sequence or pattern of RF energy, optionally coordinated with one or more magnetic field gradients (e.g. a slice- or slab-select gradient) superimposed on the base magnetic field B0 and coordinated with the RF pulses to localize or provide spatial selectivity to the RF effects (excitation and/or readout) appropriately.

The image acquisition pulse sequence provided by the exemplary MR system can include, e.g., a quantitative imaging of perfusion using a single subtraction, second version (QUIPPSII) sequence with thin-slice TI1 periodic saturation (Q2TIPS). Such pulse sequence can include (in time-sequential order) a pre-saturation pulse, an adiabatic labeling or control pulse, an appropriate delay after the label/control pulse, a plurality of periodic saturation pulses, a first background suppression pulse (which can optionally be provided during or after the periodic saturation pulses), a second background suppression pulse, several timed delays that can allow tagged blood to flow into the region being imaged as well as to control which tissue types are suppressed based on their T1 relaxation times, an EPI-based volume navigator to detect position changes, and an image data readout sequence.

Relative timing of the two inversion (suppression) pulses can be determined to suppress the correct tissue classes, and a delay time to allow for tagged blood to flow from the tagging region into the volume to be imaged can be selected. Outer volume suppression can be applied directly before the image data readout sequence (e.g., a 3D GRASE image data acquisition block or a 3D segmented gradient echo EPI sequence) for maximum efficacy. Based on such timing considerations, some delays without gradient or RF activity can remain in the pulse sequence.

The volumetric EPI-based navigator (vNav) pulse with 3D encoding can be included in this tagging/saturation/suppression sequence. For example, the vNav can be provided after the periodic saturation pulses and just before the second background suppression pulse. Such incorporation of the vNav can facilitate registration of the navigator volume to a reference volume after the second background suppression pulse, and also maintain the double inversion recovery timing through a subsequent delay (prior to a subsequent readout sequence) that can provide nulling of gray and white matter signals. The vNav can be 3D encoded with a small flip angle, such that it can minimally impact image contrast.

In further embodiments, the vNav can be inserted just after the second background suppression pulse, e.g., if the subsequent delay time prior to the readout sequence is sufficient to incorporate both the acquisition of the vNav and to calculate any position changes relative to the reference position.

Following the outer volume suppression pulse, the pulse sequence can further include a readout sequence, or image data acquisition block, provided to excite spins and obtain spatially-selective readout of RF image data from the region to be imaged. This region can include tagged blood protons if an adiabatic labeling pulse was used in the first pulse sequence, or it can be a "control" without tagged protons if an adiabatic control pulse was used in the first pulse sequence.

The exemplary image data acquisition block can be, e.g., a conventional 3D gradient and spin echo (GRASE) for obtaining RF image data in the imaged region. The 3D GRASE signal readout sequence can include, e.g., a 90° excitation pulse followed by a spin echo-based sequence that includes a series of 180° refocusing inversion pulses alternated with EPI readouts of the gradient echoes. The image data can be obtained using the RF antenna and/or one or more local coils to detect the echoes. In further embodiments, the image data acquisition block can be, e.g., a conventional 3D segmented gradient echo EPI sequence.

The image data can be motion corrected in real time (e.g., prior to each image data acquisition block) based on data from the vNav preceding each such readout sequence. In certain embodiments, the tagged and control images can be motion corrected based on a root-mean-square (RMS) error technique for registering the navigator image data obtained for successive tagged and control pulse sequences. In further embodiments, the navigator image data obtained during successive tagged and control pulse sequences can be registered (to provide motion correction in real time) based on a mutual error technique.

The system can be further configured to generate a perfusion image, using the image processing unit, based on the motion-corrected perfusion image data. The image processing unit can be configured to subtract a control image from a tagged image. Such image subtraction can be achieved, e.g., by performing a voxel-by-voxel subtraction of image intensity between tagged and control images generated from successive sets of tagged and control image data.

In a further embodiment, a method for obtaining motion-corrected images of perfusion behavior in a region of a subject can be provided. The exemplary method includes generating a tagged ASL image data of a 3D volume by providing a pre-saturation pulse, a tagging pulse, background and outer volume suppression pulses, a readout sequence (e.g. a 3D gradient and spin echo (3D GRASE) image data acquisition block or the like), and a volumetric EPI-based navigator (vNav) that can be provided after the pulsed tagging sequence, e.g., directly before or after a second background suppression pulse, and prior to a delay before the image data readout sequence. The overall sequence and timing of pulses and delays can be selected, for example, to allow tagged blood to enter the 3D volume being imaged and to provide selective control of which tissue types are suppressed based on their T1 relaxation times.

Control ASL image data of the same 3D volume can then be generated using the same pulse sequence as for the tagged image data, but substituting a control pulse for the tagging pulse. Each of the tagged and control image data sets can be processed to obtain tagged and control images, respectively. Successive images can be motion corrected and aligned based on information obtained from the respective vNav data obtained during each of the control and tagged pulse sequences. The motion correction can be provided, e.g., by registering the navigator image to a previous navigator image during the delay prior to the readout sequence.

A motion-corrected image of perfusion in the 3D volume can then be generated by subtracting the control image from the tagged image to eliminate background signals and motion artifacts, where such images can be based on image data obtained successively. Such subtraction can be performed, e.g., by calculating a voxel-by-voxel difference in the intensities of the two images.

In a further embodiment, this entire procedure of obtaining motion-corrected perfusion images can be repeated an arbitrary number of times to generate further perfusion images over a larger region of the subject and/or to increase SNR through signal averaging.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Figure 1:
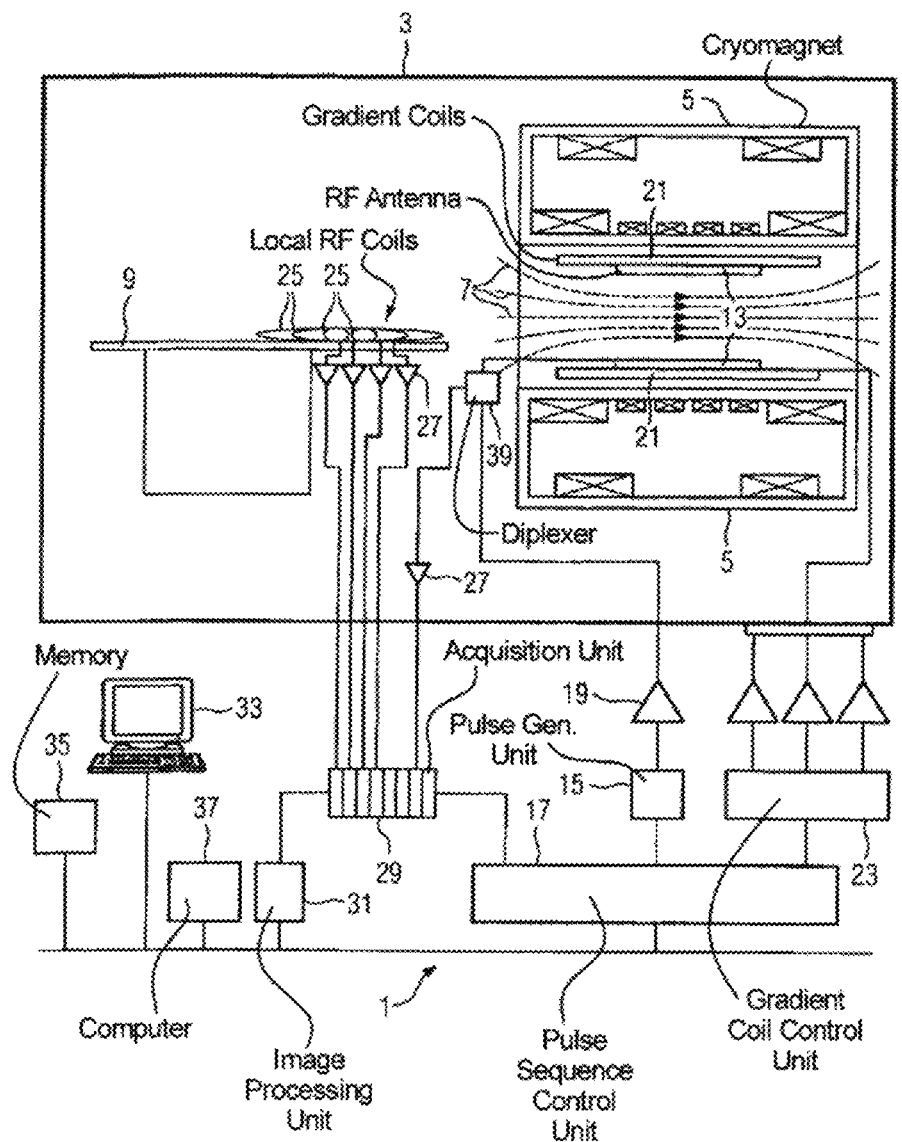
FIG. 1 schematically illustrates the basic components of a magnetic resonance imaging system constructed and operating in accordance with embodiments of the present disclosure.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

The present disclosure relates to methods and systems for providing real-time motion correction during 3D ASL perfusion MR imaging using volumetric navigators. FIG. 1 schematically shows the design of a magnetic resonance system 1 with certain components in accordance with embodiments of the present disclosure. The MR system 1 is configured, inter alia, to provide various magnetic fields tuned to one another as precisely as possible in terms of their temporal and spatial characteristics to facilitate examination of portions of a subject's body using magnetic resonance imaging techniques.

A strong magnet 5 (typically a cryomagnet) having a tunnel-shaped opening is provided in a radio-frequency (RF) shielded measurement chamber 3 to generate a static, strong base magnetic field 7. The strength of the base magnetic field 7 is typically between 1 Tesla and 3 Tesla, although lower or higher field strengths can be provided in certain embodiments. A body or a body part to be examined (not shown) can be positioned within the substantially homogeneous region of the base magnetic field 7, e.g., provided on a patient bed 9.

Excitation of nuclear spins of certain atoms within the body can be provided via magnetic RF excitation pulses that are radiated using an RF antenna 13, such as a body coil. Other configurations of RF coils or antennas can also be provided in further embodiments, and such configurations may be adapted for particular portions of the subject anatomy to be imaged. The RF excitation pulses are generated by a pulse generation unit 15 that is controlled by a pulse sequence control unit 17. After an amplification by a radio-frequency amplifier 19, the RF pulses are relayed to the RF antenna 13. The exemplary RF system shown in FIG. 1 is a schematic illustration, and particular configurations of the various components may vary from that illustrated in exemplary embodiments of the disclosure. For example, the MR system 1 can include a plurality of pulse generation units 15, a plurality of RF amplifiers 19, and/or a plurality of RF antennas 13 that may have different configurations depending on the body parts being imaged.

The magnetic resonance system 1 further includes gradient coils 21 that can provide directionally and temporally varied magnetic gradient fields for selective excitation and spatial encoding of the RF signals that are emitted and/or received by the RF antenna(s) 13. The gradient coils 21 are typically oriented along the three primary axes (x- y- and z-directions), although other or additional orientations may be used in certain embodiments. Pulsed current supplied to the gradient coils 21 can be controlled by a gradient coil control unit 23 that, like the pulse generation unit 15, is connected with the pulse sequence control unit 27. By controlling the pulsed current supplied to the gradient coils 21, transient gradient magnetic fields in the x-, and z-directions can be superimposed on the static base magnetic field B0. This makes it possible to set and vary, for example, the directions and magnitudes of a slice gradient magnetic field Gs, a phase encode gradient magnetic field Ge, and a read (frequency encode) gradient magnetic field Gr, which can be synchronized with emission and detection of RE pulses. Such interactions between RF pulses and transient magnetic fields can provide spatially selective excitation and spatial encoding of RF signals.

RF signals emitted by the excited nuclear spins can be detected by the RF antenna 13 and/or by local coils 25, amplified by associated radio-frequency preamplifiers 27, and processed further and digitized by an acquisition unit 29. In certain embodiments where a coil 13 (such as, for example, a body coil) can be operated both in transmission mode and in acquisition mode (e.g., it can be used to both emit RF excitation pulses and receive RF signals emitted by nuclear spins), the correct relaying of RF energy is regulated by an upstream transmission-reception diplexer 39.

An image processing unit 31 can generate one or more images based on the RF signals that represent image data. Such images can be presented to a user via an operator console 33 and/or be stored in a memory unit 35. A processor arrangement 37 can be configured to control various individual system components. For example, the processor arrangement 37 can be configured by programmed instructions to control such components to generate particular sequences of RF pulses and magnetic field variations according to exemplary embodiments of the disclosure described herein.

Figure 2:
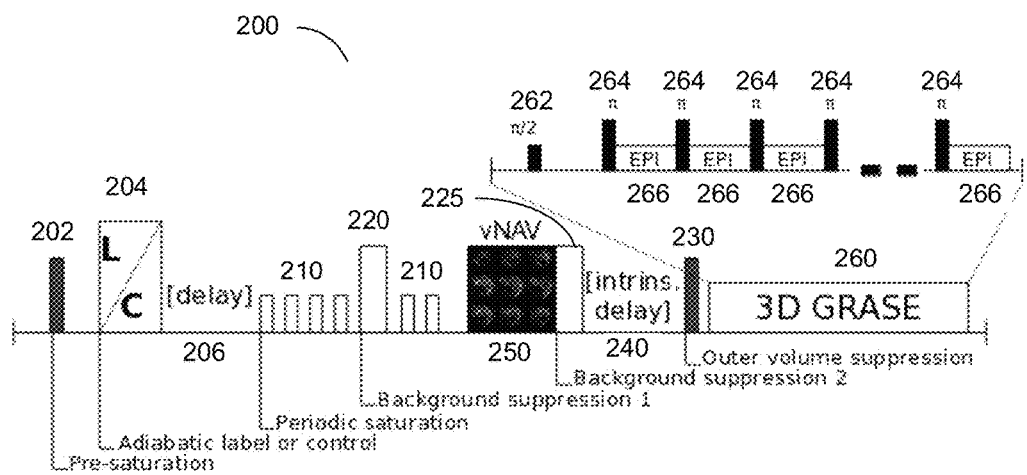
FIG. 2 is an illustration of an exemplary RF pulse sequence for ASL imaging and 3D GRASE readout that includes a 3D navigator for motion correction.

Embodiments of the present disclosure can provide motion-corrected perfusion MR imaging using an exemplary RF pulse sequence 200 as shown in FIG. 2, which includes a pulsed ASL (PASL) sequence. This sequence 200 can be provided by the system 100 shown in FIG. 1 to generate images showing perfusion activity in a region of a subject. An image data acquisition block (e.g. a readout sequence) 260, such as a 3D gradient and spin echo (GRASE) sequence or the like, can be provided for readout of the image data. Certain features and advantages of a 3D GRASE sequence for ASL imaging of perfusion are described, e.g., in W. M. Luh et al., QUIPSS II with thin-slice TI1 periodic saturation: a method for improving accuracy of quantitative perfusion imaging using pulsed arterial spin labeling, Magnetic Resonance in Medicine, 41(6):1246-54 (1999).

The exemplary RF sequence 200 includes one or more conventional in-plane pre-saturation pulses 202, followed by an adiabatic labeling (tagging) or control pulse sequence 204, which is configured to provide an inversion of arterial blood water proton spins in a region of the subject containing blood flowing into the region to be imaged. For example, the labeling pulse 204 can have a form of a sech pulse. The longitudinal magnetization from such labeling or tagging can have a long T1 decay (e.g. about 1500 ms), allowing sufficient time for the blood that is tagged upstream to enter the tissue of interest and affect subsequent imaging of this tissue.

After an appropriate delay 206, a plurality of periodic saturation pulses 210 can be provided. The saturation pulses 210 can be thin-slice pulses localized to the distal portion of the tagged region. Such periodic thin-slice pulses 210 can provide better homogeneity of the local magnetic field within a slice (as compared to a single thick-slice saturation pulse), and also provide a better match to the edges of the profile of the inversion pulse 204. The partial sequence of pulses 202, 204, 210 include conventional ASL pulses, and FAIR Q2TIPS pulses to selectively tag blood protons within a 3D source volume below the region to be imaged, saturate unwanted spins outside of this 3D volume.

First and second background suppression inversion pulses 220, 225 are also provided before the image data readout sequence 260, to reduce the amplitude of static signals. The first background suppression pulse 220 can be applied during the series of periodic saturation pulses 210. The second background suppression pulse 225 can be applied after the series of periodic saturation pulses 210, and can be configured to maintain a double inversion recovery timing for nulling signals from grey and white matter. The background suppression can help to reduce errors in a net subtracted signal (difference between the tagged and control spatial image data) to facilitate more reliable measurement of blood perfusion-related signals. An outer volume suppression pulse 230 can also be provided just before the image data readout sequence 260. Suppression pulses 220, 225 can be timed such that a recovering signal from predominant static tissue classes, e.g. gray matter and white matter, can be nulled at the moment when the image is acquired by the image data acquisition block 260. This timing can be based on the T1 relaxation times of these tissue types. Outer volume suppression pulses 230 are typically short and most effective immediately before image data acquisition. Accordingly, such outer volume suppression pulses can be provided directly or immediately before the start of the image data acquisition block 260.

In certain embodiments, the image data acquisition block 260 can be a 3D GRASE signal readout sequence, which begins with a 90° excitation pulse 262, followed by a spin echo-based sequence that includes a series of 180° refocusing inversion pulses 264 alternated with EPI readouts 266 of the gradient echoes. Conventional gradients for phase encoding, slice selection, and readouts can be applied during the readout sequence 260 to facilitate a filling of k-space based on the echo train of a single readout sequence 260. The signal in such an exemplary 3D GRASE readout sequence 260 can decay with a combination of T2 and a component of stimulated echoes with longer T1 decay.

In further embodiments, the readout sequence 260 can be, e.g., a conventional 3D segmented gradient echo EPI sequence. Although the readout sequence 260 in FIG. 2 is shown as a 3D GRASE sequence, a 3D segmented gradient echo EPI readout sequence can be used in the various embodiments described herein.

Embodiments of the present disclosure can provide real-time prospective motion correction between tagged and control image datasets. Such motion correction can be important in obtaining accurate perfusion information, which is based on small differences between labeled and control images due to tagging of blood proton spins that is detected during acquisition of image data. Motion correction can be achieved by introducing a volumetric EPI-based navigator (vNav) 250 with 3D encoding into the exemplary pulsed ASL sequence 200 shown in FIG. 2. In contrast to conventional navigator techniques that correct motion between images having the same magnetization history, embodiments of the present disclosure can provide prospective motion correction between the control and tagged sequences used in a PASL procedure, where the control and tagged sequences have different magnetization histories.

The vNav 250 can be 3D encoded with a small flip angle, such that it can minimally impact image contrast. It can be inserted into an intrinsic gap in the pulse sequence 200, such that additional motion correction and characterization can be achieved without increasing total acquisition time. For example, the volumetric navigator 250 can be inserted just before the second background suppression pulse 225, thus maintaining the double inversion recovery timing through the delay 240 that can provide nulling of gray and white matter signals. The delay 240 is provided such that the overall time interval between the adiabatic label or control pulse 204 and the image data acquisition block 260 can allow appropriate time for tagged blood to enter the region being imaged, and can be on the order of a few seconds. The delay 240 can also provide an appropriate time interval for nullification of signals from static tissue classes, e.g. gray matter and white matter, based on suppression pulses 220, 225, when the image data is acquired by the 3D GRASE image data acquisition block 260. With this configuration, the navigator volume can be registered to the reference volume time after the second background suppression pulse 225 (e.g. during the intrinsic delay 240), so that the following readout sequence 260 within the same pulse sequence 200 can be motion corrected. In this manner, the image data acquired during each readout sequence 260 can be motion corrected in real time, using conventional techniques for incorporating navigator information into MR image data processing procedures.

In a further embodiment, the navigator 250 can be inserted directly or substantially immediately after the second background suppression pulse 225, e.g., immediately prior to the beginning of the delay 240. In this embodiment, the resulting delay 240 following the navigator 250 is preferably long enough to allow for reconstruction of the obtained navigator image (e.g., using conventional 3D navigator techniques) and registration of such image to a reference navigator image. Such provision of the vNAV 250 following the second background suppression pulse 225 can reduce the duration of the delay 240 following the navigator 250, thereby reducing the extent of any motion that may occur between the navigator 250 and the image data acquisition block 260 (e.g., a 3D GRASE sequence). Based on factors such as total time interval between the adiabatic label/control pulse 204 and the image data acquisition block 260, calculation time for navigator reconstruction and registration, etc., the delay time 240 may be insufficient to incorporate the navigator 250 following the second background suppression pulse 225. For example, such calculation time could overlap with the outer volume suppression pulse 230. Under such conditions, it may be preferable to provide the navigator 250 directly before the second background suppression pulse 225, as shown in FIG. 2, even though this sequence configuration may allow a bit more time for movement to occur between the navigator 250 and image data acquisition block 260.

In certain embodiments of the disclosure, registration of the navigator images to correct for motion of the region being imaged can be achieved using conventional root mean square (RMS) error techniques. In further embodiments, the successive imaged volumes can be registered using a mutual information error function. Mutual information generally can provide a more robust registration when the volumes being registered have different contrasts. Although mutual information error functions typically take longer to calculate than RMS errors, they may provide better registration under certain conditions because the navigator image contrast can vary slightly between label and control conditions. A selection of which type of error technique to use for registering navigator images (e.g., RMS error or mutual information error) can be based on such factors as, e.g., the degree of expected or observed motion, the duration of the delay 240, the navigator image contrast differences resulting from the pulse sequence and navigator parameters, computational speed of the image analysis processor, etc.

The motion-corrected image data can be used in a flow-sensitive alternating inversion recovery (FAIR) approach to obtain images of perfusion behavior in the region of the subject. For example, images of a particular region can be generated that are based on either tagged blood or untagged blood (control) present in the region. RF data for a tagged image and an untagged image can be generated consecutively, using the pulse sequences and system described herein. A perfusion image can then be generated by subtracting a control image from a tagged image. Such image subtraction can be achieved, e.g., by performing a voxel-by-voxel subtraction of image intensity between the tagged and control images.

Motion correction using a 3D EPI navigator 250, as described herein, can provide real-time motion correction of image data, as the navigator can be used to correct image data obtained during the following readout sequence 260 (e.g. 3D GRASE). Accordingly, motion effects between successive tagged and control images can be reduced or eliminated, facilitating generation of more accurate perfusion difference images. The motion correction can also reduce or eliminate motion-related artifacts that can accrue when generating several sets of alternating control and tagged image data.

Figure 5:
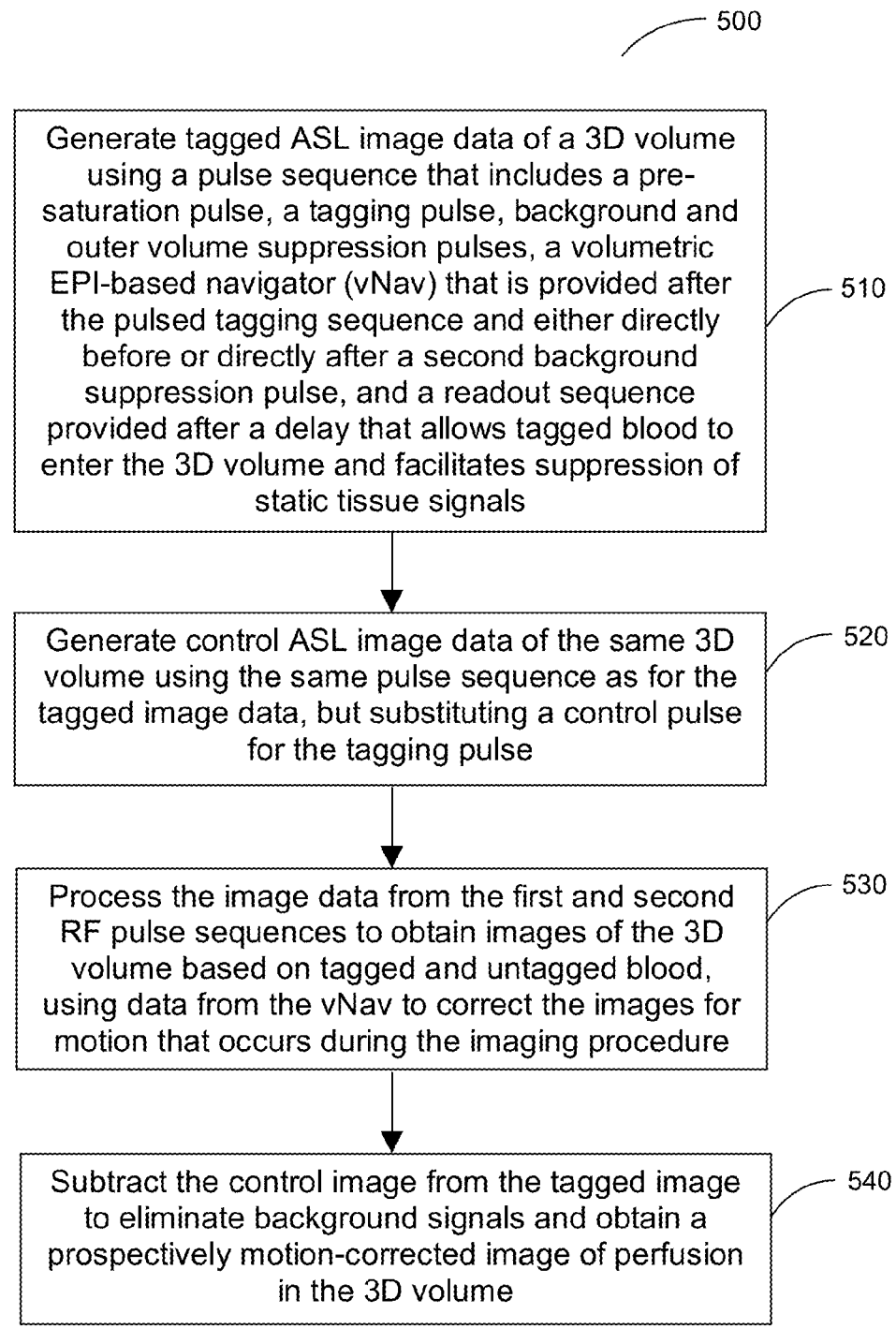
FIG. 5 is a flowchart of an exemplary motion-corrected perfusion imaging method in accordance with embodiments of the present disclosure.

An exemplary method for obtaining motion-corrected perfusion images of a 3D volume using pulsed arterial spin labeling (PASL), in accordance with further exemplary embodiments of the disclosure, is shown in the flowchart 500 of FIG. 5. In a first step 510 of the exemplary method, RF pulse sequences for obtaining tagged ASL image data of a 3D volume can be provided such as, e.g. the pulse sequence 200 shown in FIG. 2, that include a pulsed tagging sequence 210, background and outer volume suppression pulses 220, 225, 230, a readout sequence 260, and a volumetric EPI-based navigator (vNav) 250 that is provided after the pulsed tagging sequence 210, directly before the second background suppression pulse 225, and prior to a delay 240 before the readout sequence 260. The duration of the delay 240 can be selected, e.g., to allow tagged blood to flow into the 3D volume being imaged such that it is present within the imaged volume during the readout sequence 260, and to facilitate suppression of static tissue signals (e.g. white and grey matter). The readout sequence 260 can be, e.g., a 3D gradient and spin echo (3D GRASE) image data acquisition block, a 3D segmented gradient echo EPI readout sequence, or the like.

The next step 520 includes generating control ASL image data of the same 3D volume using the same pulse sequence as for the tagged image data in the preceding step, but substituting a control pulse for the tagging pulse so the blood proton spins are not tagged/labeled.

The third step 530 includes processing the image data from the tagged and control image data to obtain images of the 3D volume based on tagged and untagged blood, using data from the vNav 250 to correct the images for motion that occurs during the imaging procedure. Such motion correction can be achieved prospectively for image data obtained using each excitation/readout sequence 260 based on the preceding vNav 250.

A fourth step 540 includes subtract one image from the other, e.g., calculating a voxel-by-voxel difference in image intensity for the tagged and untagged images. Such subtraction of the images can eliminate background signals (e.g. signals arising from imaging non-blood tissue) to provide a prospectively motion-corrected image of perfusion in the imaged volume.

The method 500 can be performed using the exemplary system 100 shown in FIG. 1, where certain details of the pulse sequences and associated field gradients are described herein and/or known in the art based on the references cited herein.

Example

The system and method described herein were tested in a healthy human volunteer to assess the efficacy of the disclosed 3D navigator-based real-time motion correction for artery spin labeled imaging using a 3D GRASE readout. The imaging of blood perfusion activity in the subject's brain was done using a 3T MR scanner (MAGNETOM Skyra, Siemens Healthcare, Erlangen) with a 32 channel head coil.

A pulse sequence substantially corresponding to that illustrated in FIG. 2 was used for generating and acquiring perfusion image data. This sequence 200 includes a 3D segmented GRASE readout sequence 260 with pulsed ASL (PASL) preparation that includes flow-sensitive alternating inversion recovery with a quantitative imaging of perfusion using a single subtraction, second version, with thin-slice T1 periodic saturation (FAIR Q2TIPS), as described in the Luh et al. reference cited herein. Exemplary parameters that were used for the imaging procedure were: TR=4 s; TI=2.4 s (for gray/white matter suppression); a blood bolus duration of 700 ms; and a TE of 17.9 ms.

The tagged and control ASL perfusion images were obtained using the following exemplary resolution parameters: 64×64 matrix; a FoV of 210 ms (3.3 mm×3.3 mm); 42×3 mm axial slices; a bandwidth of 1628 Hz/px; and acquisition time $T_{acq}$ of 1:40 min:s.

The embedded 3D vNav 250 used was a 3D EPI sequence having the following exemplary pulse and resolution parameters: TR 11 ms; TE 5 ms; 32×32 matrix; 32 sagittal slices; 6/8 partial Fourier partition encoding; 8 mm×8 mm×8 mm voxels; a bandwidth (BW) of 4734 Hz/px; and acquisition time $T_{acq}$/nav of 275 ms.

To illustrate the effectiveness of the navigator sequence, a region of the brain of the subject was imaged using a conventional sequence without navigators, and a modified sequence with navigators in accordance with embodiments of the present disclosure, with and without motion correction, both in a stationary position and while deliberately moving.

Figures 3A, 3B:
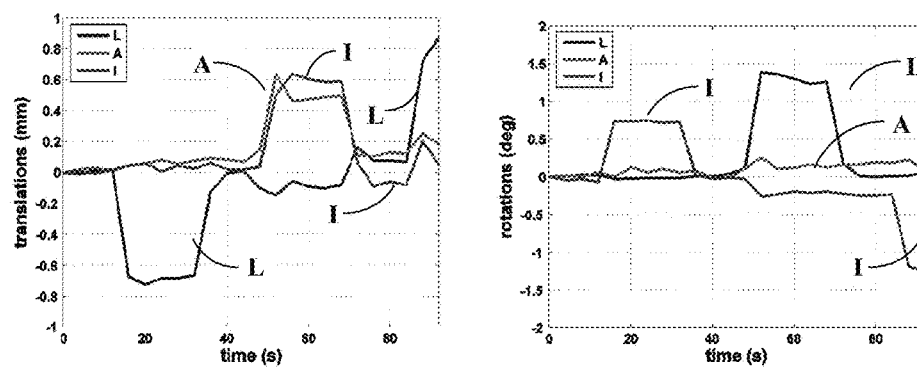
FIG. 3A is a data plot representing a deliberate translational motion of a head region that was imaged in accordance with exemplary embodiments of the present disclosure.
FIG. 3B is a data plot representing a deliberate rotational motion of a head region that was imaged in accordance with exemplary embodiments of the present disclosure.

FIGS. 3A and 3B show detected rotation and translation parameters, respectively, that were obtained during the image data acquisition procedures using navigator-based motion tracking. The rotation and translation measurements were made relative to the anterior (A), left (L), and inferior (I) directions. The deliberate motion was qualitatively similar during all scans. This motion was measured using navigators incorporated into the pulse sequence as described herein, whether or not motion correction was applied during subsequent acquisition and processing of the RF signal data.

Figure 4A:
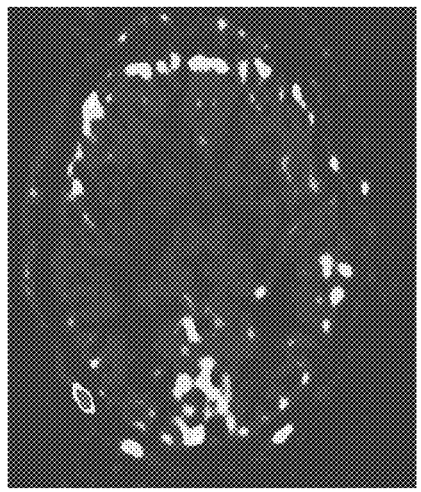
FIG. 4A is an MR perfusion image of a region of a brain obtained with no deliberate motion and no navigator-based motion correction.
Figure 4B:
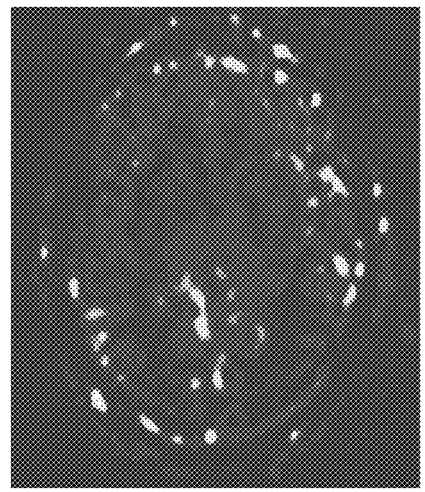
FIG. 4B is an MR perfusion image of the region of the brain shown in FIG. 4A that was obtained with no deliberate motion using navigator-based motion correction.
Figure 4C:
FIG. 4C is an MR perfusion image of the region of the brain shown in FIG. 4A obtained with deliberate motion as shown in FIGS. 3A-3B and no navigator-based motion correction.
Figure 4D:
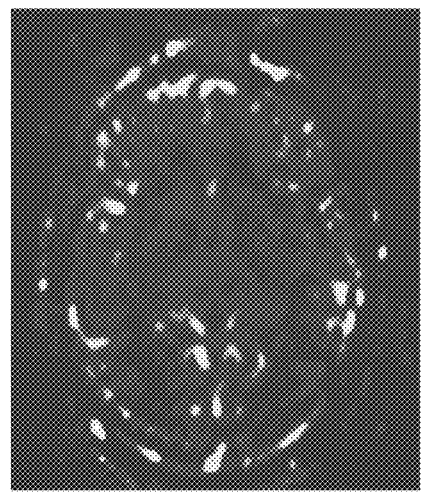
FIG. 4D is an MR perfusion image of the region of the brain shown in FIG. 4A that was obtained with deliberate motion as shown in FIGS. 3A-3B using navigator-based motion correction.

FIGS. 4A-4D show perfusion-weighted images of a cross-section of the subject's brain using the imaging parameters identified above. FIGS. 4A and 4B were obtained with no intentional motion of the subject during the image scan, and FIGS. 4C and 4D were obtained with motion during the scan corresponding to that plotted in FIGS. 2A and 2B. FIGS. 4A and 4C show perfusion images (without and with motion, respectively) obtained without a navigator pulse motion correction, and FIGS. 4B and 4D show perfusion images (without and with motion, respectively) obtained using 3D navigator-based motion correction in accordance with exemplary embodiments of the disclosure.

A comparison of FIGS. 4A and 4B, which show perfusion images obtained from a non-moving subject without and with 3D navigator motion correction, respectively, suggest that embedded vNavs provided as described herein have a negligible effect on perfusion contrast. FIG. 4C shows that motion during an ASL imaging procedure can generate considerable damage to the perfusion map, introducing significant artifacts that obscure the actual perfusion behavior. FIG. 4D shows that accurate perfusion contrast can be recovered in a scan with similar motion, by using pulse sequences that include a 3D navigator sequence and corresponding motion correction, in accordance with embodiments of the present disclosure.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure. All patents and publications cited herein are incorporated herein by reference in their entireties.

What is claimed is:

1. An MR imaging system for generating a real-time motion-corrected magnetic resonance perfusion image of a region of interest, comprising:
   an RF (Radio Frequency) signal generator and a magnetic field gradient generator configured to provide an RF pulse and magnetic field gradient sequence for acquisition of MR image data,
   said RF pulse and magnetic field gradient sequence comprising:
      a pulse sequence for selectively tagging blood protons in a volume upstream of the region of interest, the pulse sequence comprising:
         a pre-saturation pulse;
         at least one of an adiabatic tagging pulse or an adiabatic control pulse;
         a first delay followed by a plurality of periodic saturation pulses;
         a first background suppression pulse provided at least one of during and directly after a plurality of periodic suppression pulses;
         a second background suppression pulse provided after the plurality of periodic suppression pulses;
         a second delay sufficient to allow the tagged blood protons to flow into the region of interest; and
         an outer volume suppression pulse;
         3D volume navigator data generated by a 3D volume navigator following said plurality of periodic suppression pulses and at least one of directly preceding or directly following the second background suppression pulse; and
         a readout sequence for acquiring RF image data for the region of interest, and
   an image processing unit of the MR imaging system configured to:
      generate motion-corrected images based on the RF image data and the 3D volume navigator data; and
      generate a perfusion image by subtracting a first image based on a first set of RF image data obtained using the adiabatic control pulse from a second image based on a second set of RF image data obtained using the adiabatic tagging pulse.

2. The MR imaging system of claim 1, wherein the pulse sequence comprises a Q2TIPS sequence.

3. The MR imaging system of claim 1, wherein the readout sequence comprises a 3D gradient and spin echo sequence.

4. The MR imaging system of claim 1, wherein the readout sequence comprises a 3D segmented gradient echo EPI sequence.

5. The MR imaging system of claim 1, wherein the 3D volume navigator directly precedes the second background suppression pulse.

6. The MR imaging system of claim 1, wherein the 3D volume navigator directly follows the second background suppression pulse.

7. The MR imaging system of claim 1, wherein the motion-corrected images are generated based on the 3D volume navigator data using a root-mean-square (RMS) error technique.

8. The MR imaging system of claim 1, wherein the motion-corrected images are generated based on the 3D volume navigator data using a mutual information error technique.

9. A method for generating a real-time motion-corrected magnetic resonance perfusion-weighted image, comprising the steps of:
   (a) choosing an arbitrary region of interest to image;
   (b) magnetically tagging upstream blood protons outside said arbitrary region of interest to image using a pre-saturation pulse, an adiabatic label pulse, and a plurality of periodic saturation pulses;
   (c) suppressing background signals using first and second background suppression pulses;
   (d) providing a 3D echo planar imaging (EPI) navigator sequence (vNav) at least one of directly before or directly after the second background suppression pulse;
   (e) providing a delay to allow time for a tagged nuclei to perfuse into said arbitrary region of interest to image and to facilitate suppression of signals from static tissues based on the first and second background suppression pulses;
   (f) suppressing signals from an outer volume of the arbitrary region of interest to image using an outer volume suppression pulse;
   (g) collecting tagged image data using a readout sequence;
   (h) generating a tagged image of the region of interest based on the tagged image data, where an intensity of each voxel of a plurality of voxels within the arbitrary region of interest to image is decreased by any tagged blood protons that have traveled into a voxel;
   (i) generating a control image by performing the same steps (b)-(h) and substituting an adiabatic control pulse for the adiabatic label pulse;
   (j) correcting the control image and tagged image for relative motion based on vNAV data obtained for each control image and tagged image; and
   (k) creating the real-time motion-corrected magnetic resonance perfusion-weighted image by calculating a difference in intensity between the tagged image and control image on a voxel-by-voxel basis, where such difference in intensity relates to a local extent of perfusion.

10. The method of claim 9, wherein the readout sequence comprises a 3D gradient and spin echo sequence.

11. The method of claim 9, wherein the readout sequence comprises a 3D segmented gradient echo EPI sequence.

12. The method of claim 9, wherein the vNav is provided directly before the second background suppression pulse.

13. The method of claim 9, wherein the vNav is provided directly after the second background suppression pulse.

14. The method of claim 9, wherein the real-time motion-corrected magnetic resonance perfusion-weighted image are generated based on the vNAV data using a root-mean-square (RMS) error technique.

15. The method of claim 9, wherein the real-time motion-corrected magnetic resonance perfusion-weighted image are generated based on the vNAV data using a mutual information error technique.

\* \* \* \* \*